United States Patent [19]

Patel et al.

[11] Patent Number: 5,078,154
[45] Date of Patent: Jan. 7, 1992

[54] OPERATING THEATRE LINEN SYSTEM

[75] Inventors: Suresh C. R. Patel, Dalgety Bay; John A. Duncan, Glenrothes, both of Great Britain

[73] Assignee: Rotecno AG, Zurich, Switzerland

[21] Appl. No.: 507,218

[22] Filed: Apr. 9, 1990

[51] Int. Cl.⁵ .............................................. A61C 13/00
[52] U.S. Cl. ..................................... 128/849; 128/855
[58] Field of Search ............................... 128/849–855; 604/304, 307, 308

[56] References Cited

U.S. PATENT DOCUMENTS 4,344,999 8/1982 Gahlke ............................. 128/849
4,561,434 12/1985 Taylor ............................. 128/849

Primary Examiner—Robert A. Hafer
Assistant Examiner—Kerry Owens

[57] ABSTRACT

An operating theatre patient drape system which uses a combination of hydrophilic towels and hydrophobic drape sheets to provide operating theatre linen which has a low percentage of bacteria transferred across the fabric.

12 Claims, 1 Drawing Sheet

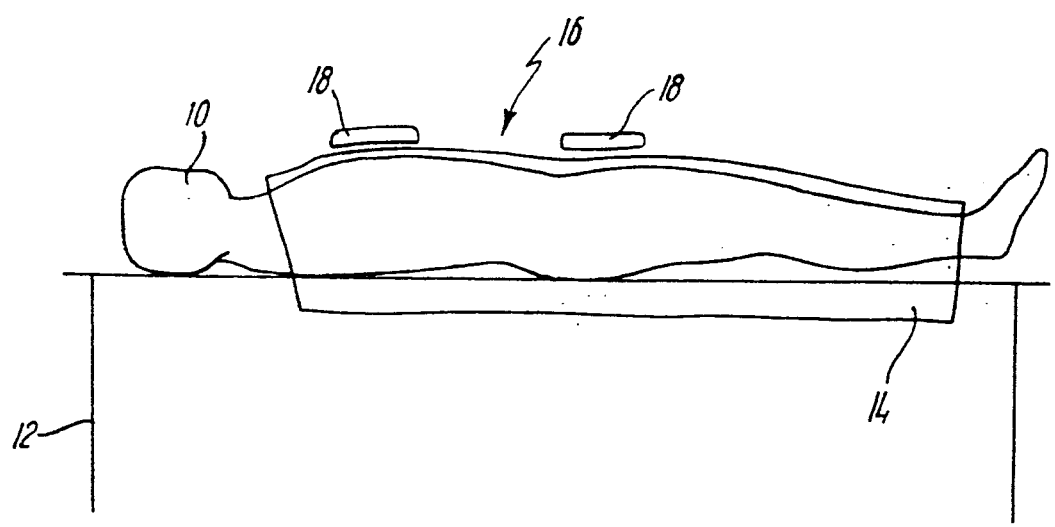

OPERATING THEATRE LINEN SYSTEM

FIELD OF THE INVENTION

This invention relates to a method of using surgical drapes in the operating theatre, and to associated linen treatment methods and products.

STATE OF THE ART

It is conventional practice in surgery to cover the patient with one or more sterile drapes such that the patient is covered substantially all over, apart from the incision site, providing a sterile barrier between the non-sterile patient and the sterile surgeon and sterile surgical instruments. The drapes are normally of woven cotton treated with a water-repellent finish. This has been found to have a number of disadvantages. One is that the water-repellent finish quickly deteriorates with laundering; this renders the drape absorbent, and it can absorb body fluids from the operation site, making it non-sterile, with the result that bacteria can be transferred to or from other parts of the patient's body and to the surgeon and to the surgical instruments. Another disadvantage is that repeated laundering and handling can, since the drape is woven from spun cotton staple, lead to relatively rapid mechanical deterioration.

The foregoing problems have led to the use of disposable water-repellent drapes. These have excellent water-repellency due to their one-time use, but are expensive and pose problems of safe disposal.

It is therefore an object of the present invention to provide an operating theatre linen system which overcomes or mitigates the above problems.

DISCLOSURE OF THE INVENTION

From one aspect the invention provides an operating theatre patient drape system comprising one or more drape sheets and one or more absorbent towels;
the or each drape sheet being formed (preferably woven) from continuous filament synthetic fabric and treated with a hydrophobic substance to provide water repellency;
the or each absorbent towel being formed (preferably woven) from continuous filament synthetic fabric and treated with a hydrophilic substance.

The synthetic fabric may be non-antistatic, or may be treated with an antistatic chemical. Most preferably the synthetic fabric is permanently antistatic.

The synthetic fabric may suitably be polyester.

Means may be provided for releasable attachment of towels to drapes during use, for example press-stud fasteners or "Velcro" (Trade Mark) type fasteners or water-soluble double-sided adhesive tape or any special fixers already in hospital use.

The absorbent towels may be permanently attached to the drape sheets by means of an adhesive which will withstand the rigours of use, washing and sterilisation.

From another aspect, the invention provides a method of using the foregoing drape system, in which the drape sheets and towels are laundered between each use, and in which at least some of the launderings comprise as the last step thereof a final rinse with water to which has been added said hydrophobic substance or said hydrophilic substance, respectively.

Preferably, the hydrophobic substance is "ROPHOBO" (Trade Mark) and the hydrophilic substance is "ROPHILO" (Trade Mark), both available from Rotecno AG of Steinstrasse 35, CH-8045, Zurich, Switzerland.

DESCRIPTION OF PREFERRED EMBODIMENT

An embodiment of the invention will now be described, by way of example only, with reference to the accompanying drawing in which the single figure illustrates schematically the invention in use.

A patient 10 supported on an operating table 12 is covered by a drape 14. The drape 14 covers substantially the whole of the patient's body except for the operation site, which is indicated generally at 16, where a suitable aperture (not seen in the figure) is provided in the drape 14. Absorbent towels 18 are disposed on the drape 14 around the operation site 16.

The drape 14 is woven from continuous filaments of polyester (or other synthetic fibre). The polyester filaments are preferably flat, but may be texturised or crimped if desired. After weaving, the fabric may be treated to provide anti-static properties in known manner, if desired.

"ROTECNO" Medical Fabric is an example of a suitable fabric which may be used for the drapes and towels. This has a pore size radius of from 15–18 microns (average 16 microns) and an air permeability of 1.98 cc/cm$^2$×sec at 0.98 mbar in accordance with British Standard BS5636. Skin particles vary in size between 7–20 microns (Journal of Hygiene, Cambridge 81, 471–479) and can carry several hundreds of thousands of bacteria. All theatre personnel and patients shed skin particles containing bacteria.

The drape is then treated to render it water-repellent, by coating with a hydrophobic substance. The preferred method is by immersion in an aqueous solution of "ROPHOBO" followed by drying. The treated drape is water-repellent, not waterproof; that is, water and water-based substances placed on the drape will lie on the surface, but could be forced into and through the drape under pressure. This construction allows steam to penetrate the fabric for more effective sterilisation.

The towels 18 are formed from the same base fabric, but are treated with a hydrophilic substance to render them absorbent. The preferred method is by immersion in an aqueous solution of "ROPHILO" followed by drying.

In use, the drape 14 is placed over the patient, and the towels 18 are arranged around the aperture over the operation site 16. Body fluids resulting from the surgical procedure lie on top of the drape 14 and their spread is limited by the towels 18 which can be replaced if they become saturated. The towels 18 may simply be placed in position; alternatively, releasable fastening means may be provided for securing the towels, such as press-stud or "Velcro" (Trade Mark) type fasteners; or permanently secured by means of suitable adhesives which will withstand the rigours of use, washing in commercial laundry equipment and steam (or other) sterlisation.

After use the drape 14 and towels 18 are washed and sterilised by normal laundry procedures. It has been found that the hydrophobic and hydrophilic properties remain acceptable for about 30 launderings. When this performance drops below acceptable standards, the hydrophobic and hydrophilic properties can be regenerated by adding "ROPHOBO" and "ROPHILO", respectively, to the final rinse of the laundry cycle, followed by normal drying.

The use of continuous-filament synthetic material gives good resistance to degradation of the mechanical properties of the drapes and towels. Samples have been tested and found to provide in excess of 300 washes without significant deterioration.

Experimental details of various fabric tests are provided below (carried out by British Textile Technology Group, Shirley Testing Service unless otherwise stated). These tests have been carried out for comparison with standard surgical gown fabric—"balloon cloth"—which is made of cotton, and with the non-woven gown fabric used in disposable sets.

1. Aqueous bacterial barrier testing

Experiments were carried out on samples of: "ROPHOBO" treated "ROTECNO" medical fabric; "ROPHILO" treated "ROTECNO" medical fabric; a sample of both fabrics together; balloon cloth—the standard surgical gown cotton fabric; and disposable non-woven gown fabric.

Method

A disc of fabric is placed within a testing chamber so as to separate the chamber into two equal halves. Each side has sterile saline added to it, and the test side also has an appropriate dilution sample of *Staphylococcus aureus* added to it. A sample of this test side is taken to determine the bacterial count, and after a set period a sample from the other side is counted and the number of bacteria that have transferred through the fabric is determined using the agar plate count technique.

Results are shown overleaf. Numbers of bacteria are calculated as % transferred across the fabric.

| Fabric | Period | % bacteria transfer |
|---|---|---|
| "ROPHOBO" treated "ROTECNO" Medical Fabric | 10 min | 0.02 |
| "ROPHILO" treated "ROTECNO" Medical Fabric | 10 min | 0.42 |
| "ROPHOBO/ROPHILO" treated "ROTECNO" Medical Fabric | 8 h | 0.05 |
| Cotton Balloon cloth | 10 min | 1.6 |
| Disposable Non-Woven Fabric | 10 min | 0.89 |

Each of the treated "ROTECNO" fabrics performed better than cotton or disposable non-woven fabric after 10 minutes. In the case of the 8h test for a combination of the treated "ROTECNO" fabrics, as a layer concept for drapes, performance was also very good.

2. Antistatic Properties (of unwashed/washed "ROTECNO" medical fabrics)

a) Unwashed

HTM No 1 Test for surface electrical resistance

Method

The fabric is rested on an insulating sheet of plastic and two electrodes of area 1 square inch are placed on the fabric with two of their edges parallel and separated by a distance of 2 inches. Tests are done with the electrodes in line with (a) the warp and (b) the weft directions of the fabric and on both surfaces of the fabric.

The electrical resistances along the fabric surfaces are measured by means of a 20 million megohmmeter under an applied potential of 500 volts dc where possible.

The fabric was conditioned at 50±2% rh at room temperature before commencing the tests in the same conditions.

Results

| | Surface electrical resistance, ohm $\times 10^{-7}$ | | | |
|---|---|---|---|---|
| | Warp | | Weft | |
| Fabric | Front | Back | Front | Back |
| "ROTECNO" Medical Fabric | 5.3 | 5.5 | 5.5 | 4.8 |

The specified limits of resistance given in HTM No 1 are $5 \times 10^4$ to $1.0 \times 10^{11}$ ohm.

This fabric has resistances which are always within the specified range and so passes the HTM No 1 test.

b) Washed

The same test was carried out on the "ROTECNO" medical fabric after 310 wash cycles in a DHSS hospital.

Again, all of the resistances measured were within the limits of $5.0 \times 10^4$ ohm and $1.0 \times 10^{11}$ ohm which are specified in HTM No 1 test.

3. Resistance to surface wetting (spray test)

Resistance to surface wetting of "ROPHOBO" treated fabric was measured according to BS 3702:1982.
Results
Spray Rating=5 (mean)

A rating of 5 indicates no wetting of and no adherence of small drops to the sprayed surface.

4. Pore Size

Equivalent pore size radius of three types of fabric was measured according to BS3321 (Bubble pressure test).
Results

| Fabric | Radius (microns) -individual results- | | | | | mean |
|---|---|---|---|---|---|---|
| "ROPHOBO" treated "ROTECNO" Medical Fabric | 16 | 16 | 15 | 18 | 16 | 16 |
| | 18 | 15 | 17 | 15 | 15 | |
| Disposable Non-Woven Fabric | 61 | 54 | 69 | 65 | 66 | 59 |
| | 59 | 55 | 62 | 53 | 53 | |
| Cotton Balloon Cloth | 60 | 53 | 59 | 59 | 61 | 59 |
| | 56 | 61 | 59 | 64 | 60 | |

As noted earlier, skin particles vary in size between 7-20 microns. Balloon cloth has a pore size radius of 59 microns and disposable single use cloth a pore size radius of 59 microns. The "ROPHOBO" treated Medical Fabric therefore has efficient filtration properties for the removal of bacteria-containing skin particles.

5. Air-borne linting properties

Air-borne linting property was measured according to the principles of BS6909:1988. The particles of lint generated after flexing the cloth were sized and counted.
Results

| Fabric | No particles > 5 microns individual results | | | | mean |
|---|---|---|---|---|---|
| "ROPHOBO" treated "ROTECNO" Medical Fabric | 303 | 177 | 194 | 290 | 241 |
| Disposable Non-Woven Fabric | 2043 | 2725 | 2706 | 1823 | 2323 |
| Cotton Balloon Cloth | 714 | 1304 | 1425 | 1348 | 1198 |

The "ROPHOBO" treated fabric had the lowest count of particles generated which were greater than 5 microns in size. Small size particles are incapable of carrying bacteria so it is important that no large size particles come from the textiles used. This is a problem with cotton fabrics.

6. Wettability

Wettability of "ROPHOBO" treated fabric was measured according to BS4554.

Results: Mean >200 sec

All the individual results of wetting time (in seconds) were greater than 200. A fabric is considered unwettable if its wetting time is greater than 200 sec. This is an important property of the "ROPHOBO" treated fabric as it must be water-repellent.

7. Air permeability

Air permeability of "ROPHOBO" treated fabric was measured according to BS 5636.

Results

| Air permeability (cc/cm$^2$ × sec at 0.98 mbar) | | | | | |
|---|---|---|---|---|---|
| -individual results- | | | | | mean |
| 1.95 | 1.81 | 2.17 | 2.05 | 1.93 | 1.98 |

8. Air-borne bacterial barrier properties

The "ROPHOBO" treated fabric was tested as follows:

Method

The apparatus consists of a perspex box (I.D. 290 mm × 290 mm) with a lid. Half way up one of the faces of the box are located two 25 mm diameter holes, 120 mm apart; another 25 mm diameter hole is located centrally, 20 mm from the top of this face of the box. For each test, two Delrin open filters holders (Gelman Science Inc.) were fitted with 25 mm membrane filters (pore size 0.8 mm). In one filter holder, a 25 mm diameter circle of test material was placed over the membrane filter, but separated from the membrane by a rubber O-ring seal. The filters were then sterilised in an autoclave at 121° C. for 15 min.

A 16h culture of *Staphylococcus aureus*, grown in tryptone soya broth, was diluted with sterile saline such that its $OD_{530}=0.1$ to 0.2. A further dilution (1 in 10,000) of this diluted bacterial broth was used for the actual tests.

The perspex box was placed in a laminar flow biological safety cabinet and the two sterile filters placed inside the box and sealed, face inwards, over the 25 mm holes half way up the face of the box. The lid was placed on the box and air (flow rate 750 ml cm$^{-2}$ min$^{-1}$) drawn through the filters. An aerosol of the previously prepared diluted *S.aureus* suspension was introduced into the box via the hole at the top of the face, by means of a Whatman chromatography spray; the spray was activated for 2 sec. After 60 sec, the airlines to the filters were disconnected, the membrane filters aseptically removed from the filter holders and placed on tryptone soya agar plates. The number of colonies on each filter membrane was determined after overnight incubation at 30° C. and the percentage of bacteria that passed through the test material was calculated.

Results

| | Bacterial Transfer % |
|---|---|
| "ROPHOBO" Treated "ROTECNO" | 0.4 |
| Medical Fabric | 0.0 } 0.1 ± 0.5 |
| | 0.0 |

A bacterial transfer of about 45% is recorded when a standard cotton balloon fabric is used. The "ROPHOBO" treated fabric exhibited a bacterial transfer of only 0.1%; indeed, in two of the three experiments carried out, no bacteria at all were able to pass through the fabric.

This fabric, therefore, is an excellent barrier to bacteria-containing skin particles under the experimental conditions employed.

9. Steam Sterilisation (carried out by the Scottish Health Service)

Brief tests were carried out using packs and trays covered with "ROTECNO" Tray Wrap samples, during yearly revalidation testing of a British Sterilizer Co. 10 cubic feet, Porous Load autoclave.

Thermocouple wires were introduced into the packs and trays, where possible duplicating these in normally wrapped packs/trays, to compare temperatures. These tests were intended to check the effect on steam presentation, drying and general ease of use.

Methods a) "Bowie-Dick" Small Load Test Packs

Two test packs were made up using 30 normal huckaback towels, both packs with thermocouples in the centre and bottom.

Pack A Normal test pack, tied together, as HTM10.
Pack B Wrapped in small "ROTECNO" wrap and taped.

A normal cycle was run and temperatures monitored. Both packs showed instant steam penetration and steady-state temperature held at 135.8°-136° C. for 3 mins 45 sec.

b) Hospital "Minor" Theatre Trays

Two identical theatre trays were processed again with thermocouples inside each.

Tray A Normal double-wrap with cotton wraps.
Tray B Double wrapped-Inner Green "ROTECNO" Outer Blue "ROTECNO"

A normal cycle was run and both trays showed instant steam penetration, with steady-state temperature of 135.5°-136° C. for 3 mins 35 sec.

At the end of the cycle, both trays were unwrapped and the contents found to be hot and dry even immediately after opening.

No problems were experienced with steam penetration and hence temperature attainment, or with drying. No obvious shrinkage took place during these limited tests. Again normal hospital use will prove this.

This material should cause no sterilisation problems in use as a wrap for steam-sterilisable trays or packs.

The above results all illustrate that "ROTECNO" fabric provides a unique combination of properties in a hospital. The fabric is completely acceptable for processing in existing equipment as used by medical industry. As it is synthetic it is very durable, light weight and easy to wash, with low energy usage to dry.

The fabric also allows evaporation of moisture (perspiration vapour), through the fabric allowing the patient's thermo-regulatory system to function.

"ROPHOBO" is chemically a water-miscible wash additive containing a non-ionic perfluoroalkyl resin which gives water-repellent properties when added to the rinse during washing.

"ROPHILO" is chemically a water-miscible wash additive containing a hydrophilic copolymer.

Water absorbency is obtained by producing a hydrophilic surface in the ultrafine textile structure so liquid is absorbed by capillary action.

The invention thus provides an operating theatre linen system which gives a high performance coupled with low costs given by repeated use.

Modifications and improvements may be made without departing from the scope of the invention.

We claim:

1. An operating theatre patient drape system comprising at least one drape sheet and at least one absorbent towel;
   said drape sheet being formed from a first woven continuous filament wholly synthetic fabric and treated with a hydrophobic substance to provide water repellency;
   said absorbent towel being formed from a second woven continuous filament wholly synthetic fabric and treated with a hydrophilic substance;
   said towel in use being releasably associated with said sheet on an exterior surface of said drape sheet relative to said patient.

2. An operating theatre patient drape system as claimed in claim 1, in which at least one of said first and second synthetic fabrics in non-antistatic.

3. An operating theatre patient drape system as claimed in claim 1, in which at least one of said first and second synthetic fabrics is treated with an antistatic chemical.

4. An operating theatre patient drape system as claimed in claim 1, in which at least one of said first and second synthetic fabrics is permanently antistatic.

5. An operating theatre patient drape system as claimed in claim 1 wherein at least one of said first and second synthetic fabrics is woven from continuous filaments.

6. An operating theatre patient drape system as claimed in claim 5, wherein said filaments are flat.

7. An operating theatre patient drape system as claimed in claim 5, wherein said filaments are textured.

8. An operating theatre patient drape system as claimed in claim 1, wherein at least one of said first and second synthetic fabrics is treated to provide antistatic properties.

9. An operating theatre patient drape system as claimed in claim 1, wherein at least one of said first and second synthetic fabrics is polyester.

10. An operating patient drape system as claimed in claim 1, wherein means of releasable attachment of said towel to said drape are provided.

11. A method of using an operating theatre patient drape system comprising at lest one drape sheet and at least one absorbent towel;
    said drape sheet being formed from a first woven continuous filament wholly synthetic fabric and treated with a hydrophobic substance to provide water repellency;
    said absorbent towel being formed from a second woven continuous filament wholly synthetic fabric and treated with a hydrophilic substance, the method comprising laundering said drape sheet and said towel between each use and in which method at least some of said launderings comprise, as a last step thereof, a final rinse with water to which has been added said hydrophobic substance or said hydrophobic substance, respectively.

12. A method as claimed in claim 11, wherein said hydrophobic substance is a water-miscible wash additive containing a non-ionic perfluoroalkyl resin which gives water-repellent properties when added to said rinse during washing and said hydrophilic substance is a water-miscible wash additive containing a hydrophilic copolymer.

* * * * *